United States Patent [19]
Bartel et al.

[11] Patent Number: 5,722,393
[45] Date of Patent: Mar. 3, 1998

[54] EXHALED GAS COOLING DEVICE

[75] Inventors: Lawrence P. Bartel, Indianapolis; Jeffery A. Attwood, Mooresville, both of Ind.

[73] Assignee: Methodist Hospital of Indiana, Inc., Indianapolis, Ind.

[21] Appl. No.: 141,420

[22] Filed: Oct. 20, 1993

Related U.S. Application Data

[63] Continuation of Ser. No. 869,955, Apr. 17, 1992, abandoned, which is a continuation of Ser. No. 497,558, Mar. 22, 1990, abandoned.

[51] Int. Cl.$^6$ .............. A61M 16/00; A62B 7/00; F24F 5/00; F16K 31/00
[52] U.S. Cl. .............. 128/204.15; 128/204.23
[58] Field of Search .............. 128/204.16, 204.18, 128/204.26, 205.12, 911, 912, 204.15, 204.23

[56] References Cited

U.S. PATENT DOCUMENTS

| | | | |
|---|---|---|---|
| 2,502,263 | 3/1950 | Lewis | 128/204.15 |
| 2,702,546 | 2/1955 | Gilroy et al. | 128/204.16 |
| 2,852,022 | 9/1958 | Netteland | 128/204.15 |
| 2,920,622 | 1/1960 | Steel | 128/204.16 |
| 3,090,382 | 5/1963 | Fegan et al. | 128/204.16 |
| 3,592,191 | 7/1971 | Jackson | 128/204.16 |
| 3,603,313 | 9/1971 | Arblaster | 128/205.12 |
| 3,646,934 | 3/1972 | Foster | 128/204.16 |
| 3,961,627 | 6/1976 | Ernst et al. | 128/204.26 |
| 4,080,103 | 3/1978 | Bird | 128/204.16 |
| 4,446,869 | 5/1984 | Knodle | 128/205.12 |
| 4,456,008 | 6/1984 | Clawson et al. | 128/205.12 |
| 4,462,398 | 7/1984 | Durkan et al. | 128/204.26 |
| 4,619,269 | 10/1986 | Cutler et al. | 128/204.16 |
| 4,653,493 | 3/1987 | Hoppough | 128/205.12 |
| 4,727,871 | 3/1988 | Smargiassi et al. | 128/205.12 |
| 4,867,153 | 9/1989 | Lorenzen et al. | 128/205.12 |
| 4,905,685 | 3/1990 | Olsson et al. | 128/205.12 |
| 4,924,860 | 5/1990 | Larsen et al. | 128/205.12 |
| 4,938,212 | 7/1990 | Snook et al. | 128/205.24 |

FOREIGN PATENT DOCUMENTS

| 2079984 | 1/1982 | United Kingdom | 128/204.26 |
|---|---|---|---|

OTHER PUBLICATIONS

"Ventilators Theory and Clinical Application." Dupuis, the C.F. Mosby Company, 11830 Westline Industrial Drive, St. Louis, Missouri 63146, pp. 481–500 (1986).

*Primary Examiner*—K. B. Asher
*Attorney, Agent, or Firm*—Woodard, Emhardt, Naughton, Moriarty & McNett

[57] ABSTRACT

An improved ventilator apparatus and method includes a ventilator having an inspiration side for delivery of air to a patient and an expiration side for receiving air from the patient, the expiration side including an air flow path through the ventilator for monitoring of the expired air, a first conduit connecting the inspiration side of the ventilator to the patient, a second conduit communicating expiration air from the patient to an air cooler, and a third conduit coupling the outlet of the air cooler to the air flow path on the expiration side of the ventilator, the air cooler operating to cool the expired air to a temperature sufficiently low as to eliminate moisture condensation as the expired air passes through the flow path on the expiration side of the ventilator. The expired air is preferably cooled to about or below the temperature within the expiration side flow path.

32 Claims, 2 Drawing Sheets

EXHALED GAS COOLING DEVICE

This application is a continuation of application Ser. No. 07/896,955, filed Apr. 17, 1992, now abandoned, which was a continuation of Ser. No. 07/497,558, filed Mar. 22, 1990, now abandoned.

BACKGROUND OF THE INVENTION

1. Field of the Invention

The present invention relates to ventilators for use in the medical field, and particularly to an improved ventilator apparatus and method which eliminate the deleterious effects of moisture condensation in the expiration side of the ventilator equipment.

2. Description of the Prior Art

Ventilators are used to provide respiratory air for a patient. The ventilator includes an inspiratory side which supplies air to the patient. This air may be provided under different conditions, such as controlled or supported ventilation, spontaneous ventilation or manual ventilation. Under the different circumstances, the inspiration side may monitor and/or regulate such parameters as oxygen and moisture content of the air, and volume and frequency of inspiration. The ventilator also includes an expiration side which receives the exhaled air. The expiration side is used to monitor the volume of expired air and to control ventilation of the patient. General examples of ventilating systems are contained in U.S. Pat. Nos. 3,090,382, issued to Fegan, et al. on May 21, 1963; 3,646,934, issued to Foster on Mar. 7, 1972; and, 4,080,103, issued to Bird on Mar. 21, 1978.

A problem has existed in the prior art due to the great amount of moisture in the exhaled gases. The expired air leaves the patient saturated with water vapor and at 98.6° F. or within a few degrees thereof. As this air cools, the water condenses out. The problem is encountered because the gases are passed through highly sensitive components on the expiration side of the ventilator. The condensed moisture collects on these and accumulates in the ventilator. This in turn interferes with the operation of the ventilator, and can cause significant damage to the ventilator components. There has consequently been a continuing desire for a ventilator apparatus and method which overcome the problems associated with condensation of moisture in the expiration side of the ventilator.

The condensation of water vapor can present additional problems to the operation of the ventilator. The ventilator includes a flow transducer which is used to determine the volume of gas expired by the patient. This transducer may take the form of a fine mesh screen which provides resistance to air flow. The increase in pressure resulting as the exhaled air encounters the screen is used to determine the volumetric flow. If moisture accumulates on the screen, this will present an additional barrier to air flow, resulting in false readings of the flow transducer. The air pressure downstream of the flow transducer is also used in certain instances to trigger the delivery of inspiration air to the patient. In operation, the development of negative pressure downstream of the flow transducer signals the beginning of inspiration by the patient, and the ventilator acts in response thereto. Condensate on the flow transducer screen may adversely affect this function. Also, a bacteria filter is provided in the expiration line from the patient to prevent the transmission of bacteria into the room. The collection of moisture on the bacteria filter will present a greater resistance to flow, affecting both the accuracy of the volumetric flow readings and the ease with which the patient may exhale. It is apparent that the condensation of water vapor at the filter or within the ventilator may significantly affect the desired operation of the ventilator in all of these respects.

In contrast to the present invention, the prior art approaches to this problem have been to heat the exhaled air and/or the ventilator components to prevent condensation of moisture. In at least one prior art ventilator, the flow transducer on the expiration side is heated to approximately 60° C. to reduce condensation. This unit is marketed as the Servo Ventilator 900C by Siemens-Elema AB, Ventilator Division, S-171 95 SOLNA, Sweden. While this heating will affect the amount of condensation, it will not prevent condensation at locations in the ventilator other than at the flow transducer.

Another approach in the prior art has been to provide heating of the bacteria filter located at the entrance to the expiration side of the ventilator. This unit is available under the designation "Star Exhalation Isolation System" from Infrasonics, Inc. of San Diego, Calif. Under this system, a standard bacteria filter is located in a chamber mounted immediately upstream of the expiration side of the ventilator. A heater is placed around the filter to heat the filter and inhibit condensation of moisture on the filter. Again, heating the filter and air will provide a temporary limit on condensation, but the moisture will condense subsequently in the ventilator once the air cools below its dew point temperature.

In another prior art approach, a wire is extended through the tubing which carries the exhaled air from the patient to the ventilator. The wire operates as a resistance heater to keep the air from cooling prior to entering the ventilator. This system will also inhibit condensation for the time that the air remains above its temperature upon leaving the patient. Condensation will still occur in the ventilator, however, as soon as the air has cooled below its dew point.

Earlier attempts to control the condensation problem involved keeping the gas warm throughout the length of the ventilator tubing (heated wire systems). This idea worked until it reached the ventilator flow transducer compartment whereupon the gas immediately cooled, flooding the compartment. Hydrophobic filter media prevents condensate from passing beyond the filter. Unfortunately, the media does not appreciably lower the gas temperature, so gas continues to cool and condensate forms on its way to the transducer.

In U.S. Pat. No. 4,619,269, issued to Cutler, et al. on Oct. 28, 1986, there is described a system including a standard ventilator and a separate gas monitor used for sensing components of the exhaled air. The ventilator system in Cutler provides a main flow of air which circulates directly from one side of the ventilator to the other. A portion of this main air flow is diverted to the patient as ventilating air and is then recycled back to the main flow. The air expired by the patient passes through a flow meter followed by a mixing chamber and then into the main recycle flow. No treatment is described in the Cutler patent for this expired air to prevent condensation of moisture in the ventilator. The Cutler patent describes the condensation of water vapor from a sample stream of the expired air which is fed to carbon dioxide and oxygen sensors, the purpose being to avoid interference with the analysis of the air. The sample is then exhausted from the system.

There has remained a need for a ventilating system which avoids the problems associated with condensation of water vapor in the expiration side of the ventilator. Such a system would desirably provide a simple, efficient and economical solution to this longstanding problem, and the present invention satisfies these requirements.

The advent of ventilator electronics, such as the electronic flow transducer, has brought exciting new innovations in ventilator patient management to the medical field. The flow transducer, lying in either the inspired or expired patient gas flow, offers accurate, precise measurement of patient volumes and flows previously unattainable. However, a problem with the expiratory flow transducer, most notably that which measures expired gas, has been its susceptibility to water vapor condensation which results in erroneous flow/volume information and/or premature failure. The few solutions to this problem have offered limited success. The present invention provides a simple apparatus and method for diminishing water condensation on the expired flow transducer by reducing the gas temperature before it reaches the transducer.

SUMMARY OF THE INVENTION

Briefly describing one aspect of the present invention, there is provided a ventilating system which includes a ventilator having an inspiration side and an expiration side, an inspiration conduit for directing air from the inspiration side of the ventilator to a patient, a first expiration conduit for receiving expiration air from the patient, an expiration air cooler for receiving the expiration air from the first conduit, and a second expiration air conduit for directing the cooled expiration air from the air cooler to the expiration side of the ventilator, the expiration air cooler operating to cool the air to a temperature sufficiently low to substantially eliminate further cooling of the air within the expiration side of the ventilator. The present invention also provides a related ventilating method.

It is an object of the present invention to provide an improved ventilating system and method which do not suffer the adverse effects resulting from condensation of moisture within the expiration side of the ventilator.

Another object of the present invention is to provide an improved ventilating system and method which reduces the frequency of replacing air filters associated with the expiration air.

Further objects and advantages of the present invention will be apparent from the description of the preferred embodiment which follows.

DESCRIPTION OF THE PREFERRED EMBODIMENT

Figure 1:
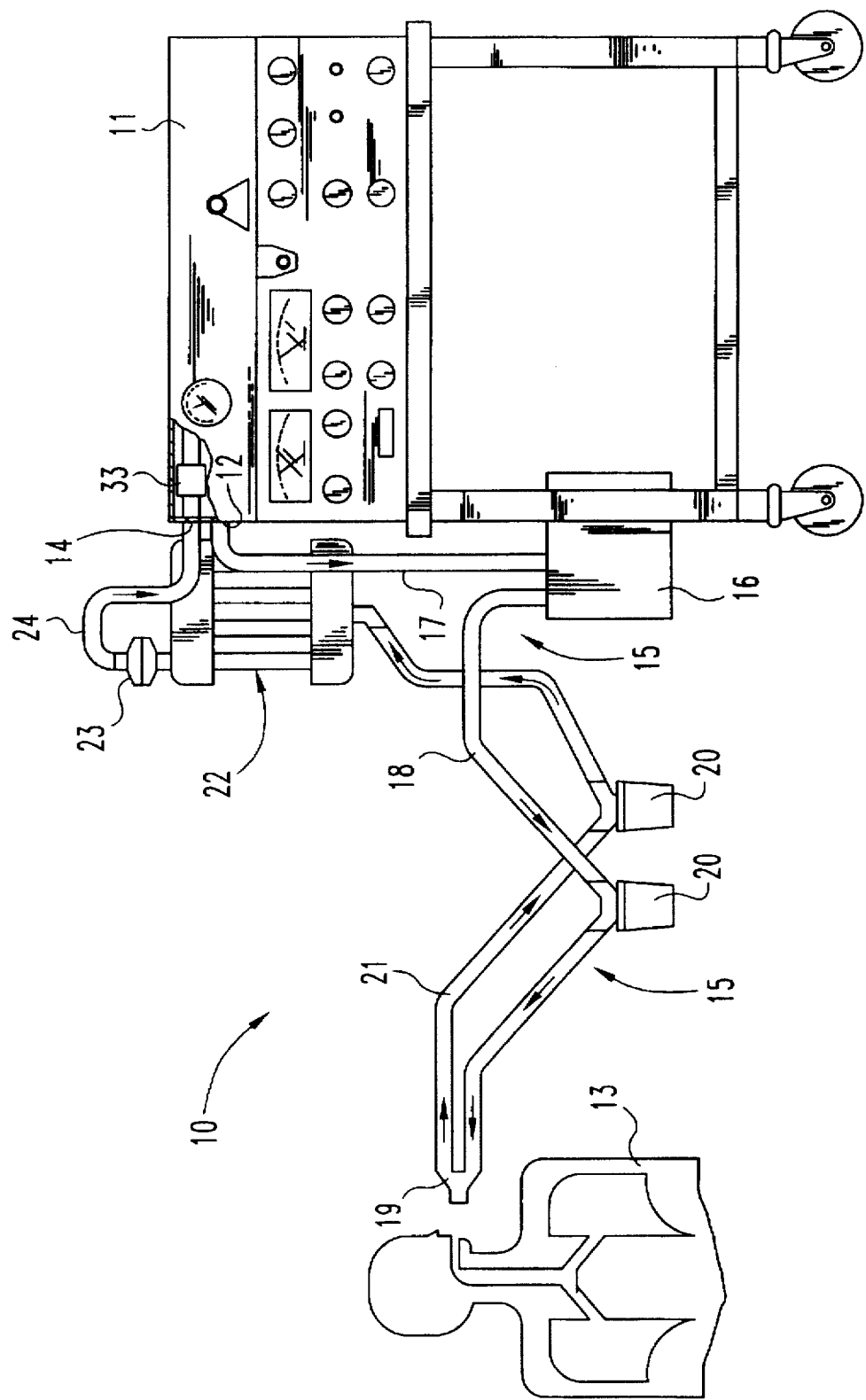
FIG. 1 is a schematic drawing showing the improved ventilating system of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention provides an improvement for ventilating systems and devices which substantially eliminates the condensation of water within the expiration side of the ventilator. Certain prior art ventilators may be described as having an inspiration side and an expiration side. The inspiration side is that portion of the ventilator which delivers inspiration air to the patient. This may include humidification of the air, heating of the air and volume control of the air.

The expired air from the patient is passed through the expiration side of the ventilator for varying purposes. The expiration side typically includes a flow transducer to permit accurate measurement of air volumes and flows. Also, the expiration air may be used to trigger the timing for the inspiration side of the ventilator. In other words, as is well known and conventional in the art, a ventilator including a flow transducer which measures air volumes is a volume-cycled ventilator in which the flow transducer measures the volumetric flow rate of the expiration air passed therethrough. Similarly, a ventilator including a flow transducer which measures air flows is a flow-cycled ventilator in which the flow transducer measures the linear flow rate of the expiration air passed therethrough. Thus, the appearance of a negative pressure at the expiration side indicates that the patient has initiated inspiration, and therefore that the ventilator should deliver the inspiration air to the patient.

These functions of the expiration side of the ventilator may be seriously compromised as a result of condensation of moisture. For example, the flow transducer may comprise a fine-mesh screen which is used to develop a back pressure upon expiration, and to thereby enable measurement of the expired air flow. The development of condensation on this screen will obviously affect the accuracy of these flow measurements. Also, the development of moisture on the screen, or on an air filter upstream of the expiration side of the ventilator, can produce increased flow resistance, thus interfering with the patient's breathing. The present invention provides a system by which the adverse effects associated with condensation of moisture are avoided.

The ability of gas to hold water vapor varies directly with its temperature, i.e., the warmer the gas the more water vapor it can hold. When a gas contains all the water vapor it can hold it is said to be "saturated". The temperature at which a gas is saturated is its dew point. As a gas cools, it loses its ability to hold as much water vapor, which condenses from the gaseous to the liquid state. Patient expired gas is at a temperature of about 37° C. and is saturated. The natural tendency of expired gas as it travels the length of the expiratory limb of the ventilator breathing circuit is to equilibrate with the ambient air which is usually about 22° C. As the gas cools, water vapor condenses, notably on the expiratory flow transducer, causing erroneous flow/volume readings and premature failure. If, however, the gas is cooled sufficiently before it reaches the transducer, little if any further condensation takes place. The present invention serves to stabilize gas temperature before reaching the sensitive gas measuring devices of the expiration side of the ventilator.

In one embodiment, the expired gas cooler consists of a specially constructed miniature radiator utilizing a high efficiency core and a 24 volt DC brushless fan wired to the ventilator via a 15 pin connector. The cooler and fan are mounted inside a stainless steel case. Power to the fan is controlled by a lighted rocker switch fitted on the case exterior. Plastic guards are installed on both sides of the fan. The cooler and fan are further protected by a reusable dust filter.

The principle of operation is similar to that of an automobile radiator except in this case gas is being cooled instead of a liquid. Exhaled gas from the patient enters into the bottom tank of the cooler via the expiratory limb of the ventilator circuit. The gas travels upwards through several channels in the high efficiency core while air is being continuously blown over the core to assist with heat dissipation. As the exhaled gas is cooled, its ability to hold water diminishes and condensation takes place. Condensate drains from the channels to the angular lower tank and into the expiratory limb of the ventilator circuit. Inline on the expiratory limb is a condensate collection trap. The cooler gas exits through the top tank of the cooler, is filtered, and enters the ventilator for measurement.

Referring particularly to the drawings, there is shown a ventilating system 10 for providing inspiration air to a patient and for receiving expiration air from the patient. The system includes a ventilator apparatus 11, which includes in conventional fashion an inspiration air side and an expiration air side. The inspiration air side 12 operates as a means for providing inspiration air for delivery to the patient 13. The expiration air side 14 receives expiration air from the patient, and operates in the manner previously described. In particular, the expiration side includes an air flow path within the ventilator apparatus, within which is located the monitoring devices such as an electronic flow transducer 33, all of which is conventional in the prior art. By way of example, a typical ventilating apparatus useful with the present invention is the Servo Ventilator 900C, available from Siemens-Elema AB, Ventilator Division, S-1719S SOLNA, Sweden.

Inspiration conduit means, shown generally at 15, connect with the inspiration air side of the ventilator 11 for communicating inspiration air to the patient. As shown in FIG. 1, a heater/humidifier 16 may be included for conditioning the inspiration air prior to delivery to the patient. Therefore, as shown, the inspiration conduit means 15 includes a first tube 17 communicating between the inspiration side 12 of the ventilator and the heater/humidifier 16/. A second tube 18 connects from the heater/humidifier to a Y-connector 19 at the patient. A water trap 20 may be included along tube 18 to collect condensed moisture.

Expiration air from the patient is returned to the expiration side 14 of the ventilator. A first expiration conduit 21 receives the expiration air from the patient and delivers it to an air cooler 22. A water trap 20 is included along the conduit 21. Expiration air then passes through the cooler 22, and an optional bacteria filter 23, and then through a second expiration air conduit 24 to the expiration side of the ventilator.

The expiration air cooler 22 operates to cool the expiration air to a temperature sufficiently low to substantially eliminate further cooling of the expiration air within the expiration side of the ventilator. In particular, the expiration air is passed eventually through a flow path in the expiration side of the ventilator in which path is located the detecting instrumentation such as the electronic flow transducer. When the expiration air is passed through this flow path, the flow path will be maintained at a given, first temperature.

It is a function of the present invention to cool the expiration air from its original temperature upon leaving the patient, to a temperature which is about at the temperature in the flow path. Therefore, further cooling of the expiration air will not occur within that flow path, and condensation of moisture will be substantially eliminated.

Some cooling of the air will occur as it passes along the conduit 21. For example, the temperature of the expiration air as it enters the cooler 22 may be about 29.5° C. In contrast, the temperature in the flow path on the expiration side 14 of the ventilator will approximate ambient temperature. Since the expired air is saturated at body temperature, any cooling will result in condensation of moisture. For the same reason, the air which is at 85° F., if it were to enter directly into the flow path on the expiration side 14, would be further cooled since the expiration side will typically be close to ambient temperature, or about 70°–75° F. The cooler 22 is therefore provided to significantly cool the expiration air below the temperature at which it would otherwise normally enter the ventilator.

The extent of cooling desired for the expiration air will depend to some extent on existent conditions. In a typical situation, the expiration air is reduced in temperature by the cooler 22 by greater than about 10° F. The cooled air is preferably within about 5° F. of ambient temperature, and is most preferably about ambient temperature. Preventing condensation of moisture would be further assured by cooling the expiration air to below ambient temperature. In terms of the temperature within the air flow path on the expiration side of the ventilator, the cooler 22 preferably operates to cool the expiration air to within about 2° F. of the flow path temperature, and most preferably to about or below the temperature in the expiration flow path of the ventilator.

Figure 3:
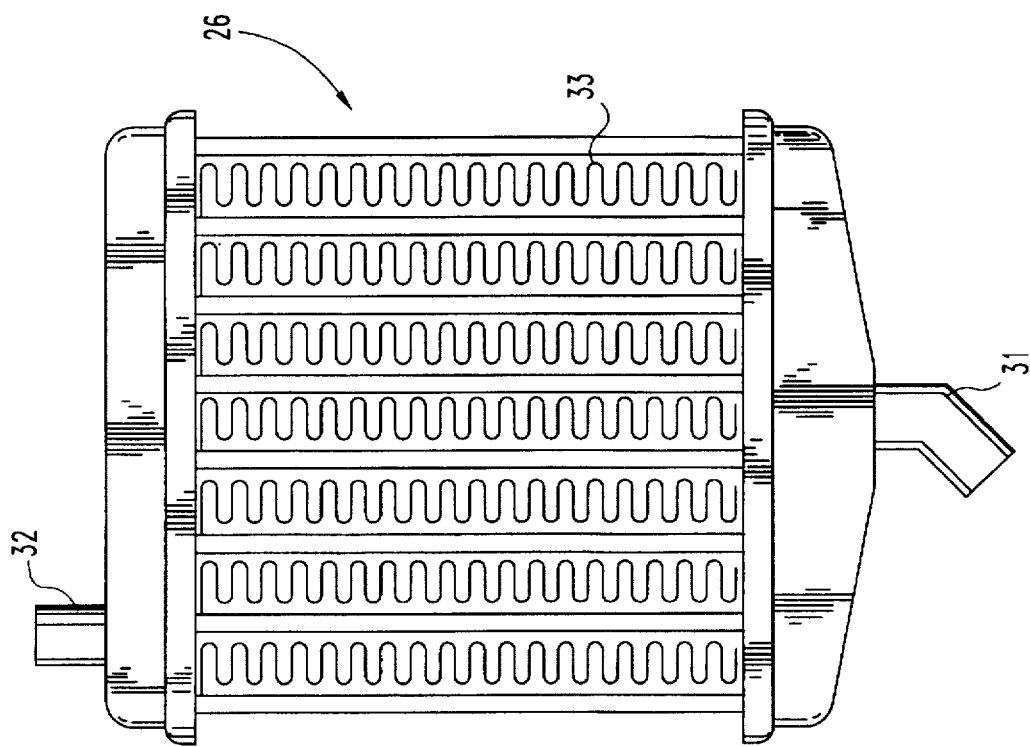
FIG. 3 is a front, elevational view of a radiator useful in the present invention.
Figure 2:
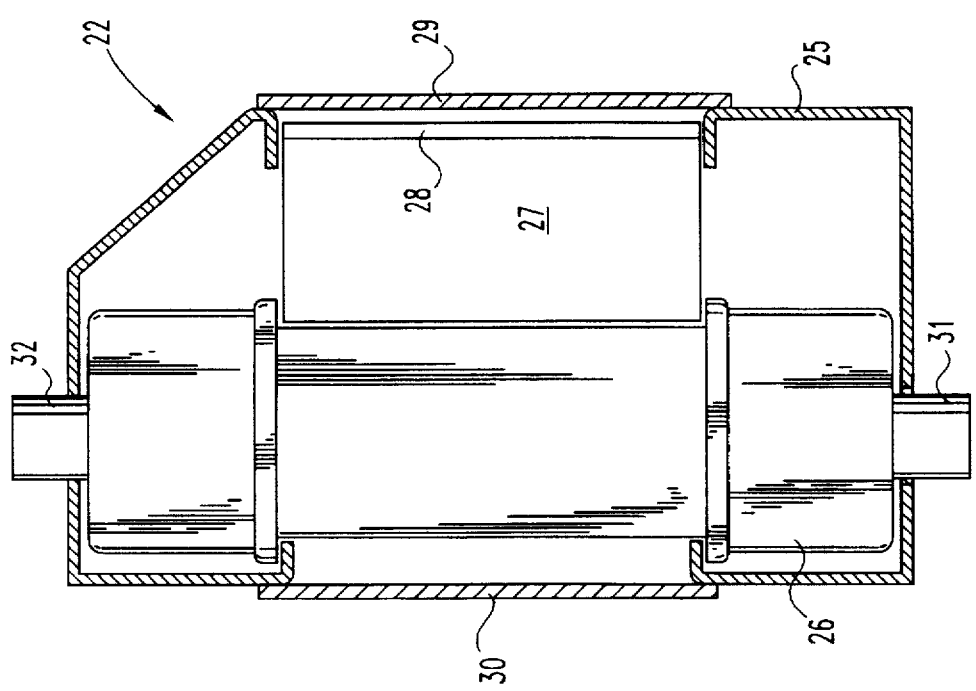
FIG. 2 is a side, cross-sectional view showing an expiration air cooling device useful with the present invention.

Referring in particular to FIGS. 2 and 3, a preferred embodiment for the air cooler 22 is shown. The air cooler comprises a case 25 within which are mounted a radiator 26, fan 27 and filter 28. Front and rear covers 29 and 30 are secured to the case 25.

The radiator 26 may be of conventional design. The radiator includes an inlet 31 to which is connected the conduit 21. The radiator further includes an outlet 32 to which is connected the conduit 24 or alternatively an air filter 23 which is in turn connected with the conduit 24. The structure of the radiator is conventional in design, with the expiration air passing from inlet 31 to outlet 32 through a tortuous path to permit cooling. Radiating fins 33 dissipate the heat and efficiency of the radiator is enhanced by operation of the fan 27 blowing air across the radiator. The radiator may be formed from a variety of materials satisfactory to the cooling operation and having adequate tolerance of the expired air. A copper or brass alloy, for example, is suitable for this purpose.

It will be appreciated that the air cooler 22 may assume a variety of alternate designs, other than a conventional radiator as shown. For example, a refrigerating unit could be used to reduce the air temperature, which would facilitate the ability to reduce the air temperature below ambient temperature or below the temperature within the flow path on the expiration side of the ventilator. Selection of an appropriate air cooler device, and sizing for the same, will depend on factors such as the volume of air to be cooled, the degree of cooling required, power utilization by the cooler, physical size, etc. The combination radiator 26 and fan 27 has been found to be useful since it provides a sufficient amount of cooling while being relatively small and inexpensive, and having low power requirements. In a preferred embodiment, the fan 27 is electrically coupled with the ventilator, and therefore may be conveniently mounted to existing ventilator devices. Suitable brackets or direct mounting of the cooler to the ventilator may be used to physically couple the two units.

To demonstrate the operation of the air cooler 22, a particular embodiment of the present invention is as follows.

A model of a normally configured expiratory limb of the ventilator test circuit was constructed with a 60 cm length of corrugated tubing attached to one port of a Travenol controller canister used as a gas source. A 183 cm length of 22 mm I.D. aerosol tubing was connected from the other port of the canister to the expiratory moisture trap of a Siemens Servo 900C ventilator (Elema-Schonander, Inc., Sweden). A Ballard safety drain (Ballard Medical Products, Midvale, Utah) was inserted 105 cm distal to the canister. A Pall BB50T filter (Pall Corporation, Glen Cove, N.Y.) was inserted between the expiratory moisture trap and the expiratory gas inlet of the Servo 900C.

A temperature-controlled gas, in this instance oxygen, was passed through the expiratory limb described in the previous paragraph. The gas temperature measured at the inlet of the cooler was allowed to stabilize at 48.8° C. (120° F.) at a flow rate of 60 lpm. Gas temperature was then measured at the outlet of the EGC and found to be 23.3° C. (74° F.) Room temperature was 72° F. Gas flow was measured to determine flow resistance. Flow resistance without the cooler installed ranged from 0.7 cm $H_2O$ at 10 lpm (+ or −0.5 lpm) to 11.6 cm $H_2O$ at 80 lpm (+ or −4 lpm). Flow resistance with the cooler installed ranged from 0.7 cm $H_2O$ at 10 lpm (+ or −0.5 lpm) to 12.8 cm $H_2O$ at 80 lpm (+ or −4 lpm).

The present invention provides several advantages. By cooling the air prior to its entry into the expiration side of the ventilator, moisture condensation is substantially eliminated, with improved accuracy of readings, greater reliability in operation of the ventilator, and reduced resistance to air flow for the patient. In addition, hydrophobic filters are routinely used to help protect the expiratory flow transducer on the Servo 900C and other ventilators. Filter replacement frequency may range in the prior art from one filter per 8-hour shift to as many as ten filters per 8-hour shift based upon patient minute volume requirements. With the present invention, filter replacement can be diminished to one filter per 24-hour period. Certain patients require high minute volumes necessitating frequent ventilator interruptions to allow filter changes. Unfortunately these patients may also be hemodynamically unstable and can become hypotensive and bradycardic the instant they are disconnected from the ventilators. The patients are therefore placed in less risk with the present invention since the frequency of interruptions is substantially reduced.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A ventilating system for providing inspiration air to a patient and for receiving expiration air from the patient, which comprises:

a flow-cycled ventilator apparatus having inspiration air means and expiration air means, the inspiration air means being for providing inspiration air for delivery to the patient, the expiration air means being for receiving the expiration air from the patient, the expiration air means including an expiration air flow path within said ventilator apparatus;

flow transducer means located within the expiration air flow path for receiving the expiration air therethrough and for measuring the linear flow rate of the expiration air passed therethrough, said flow transducer means further being for initiating the delivery of inspiration air from the inspiration air means in response to the measured linear flow rate of the expiration air;

inspiration conduit means connecting with the inspiration air means for communicating inspiration air to the patient;

first expiration conduit means for receiving expiration air from the patient;

expiration air cooling means including an expiration air cooler and being for cooling the expiration air received from the patient, said first expiration conduit means connecting with the expiration air cooler and being for communicating expiration air from the patient to the expiration air cooler; and second expiration air conduit means communicating between the expiration air cooler and the expiration air means of said ventilator apparatus for delivering air from the expiration air cooler to and through the expiration air flow path of the expiration air means and through said flow transducer means;

said expiration air cooling means being for cooling the expiration air to a temperature sufficiently low to substantially eliminate further cooling of the expiration air as it passes through the expiration air flow path of the expiration air means and through said flow transducer means, said flow transducer means thereby receiving the expiration air therethrough, measuring the linear flow rate of the expiration air passing therethrough, and initiating the delivery of subsequent inspiration air in response to the measured linear flow rate of the expiration air.

2. The ventilating system of claim 1 in which said expiration air cooling means comprises a heat exchanger.

3. The ventilating system of claim 1 in which said second expiration air conduit means includes an air filter.

4. The ventilating system of claim 1 in which said expiration air cooling means is for cooling the expiration air greater than about 10° F.

5. The ventilating system of claim 1 in which said expiration air cooling means is for cooling the expiration air to not more than about 5° F. above ambient temperature.

6. The ventilating system of claim 5 in which said expiration air cooling means is for cooling the expiration air to below ambient temperature.

7. The ventilating system of claim 1 in which the temperature within the air flow path of the expiration air means of said ventilator apparatus is at a first temperature, and in which said expiration air cooling means is for cooling the expiration air to not more than about 2° F. above the first temperature.

8. The ventilating system of claim 7 in which said expiration air cooling means is for cooling the expiration air to below the first temperature.

9. A ventilating method for providing inspiration air to a patient and for receiving expiration air from the patient, which comprises the steps of:

a. providing a flow-cycled ventilator apparatus having inspiration air means and expiration air means, the inspiration air means being for providing inspiration air for delivery to the patient, the expiration air means being for receiving and detecting the expiration air from the patient, the expiration air means including an expiration air flow path within the ventilator apparatus, said ventilator apparatus further including a flow transducer means located within the expiration air flow path for receiving the expiration air therethrough and for measuring the linear flow rate of the expiration air passed therethrough, said flow transducer means further being for initiating the delivery of inspiration air from the inspiration air means in response to the measured linear flow rate of the expiration air;

b. delivering the inspiration air from the inspiration air means to the patient;

c. receiving the expiration air from the patient and delivering the expiration air to an expiration air cooler;

d. cooling the expiration air in the expiration air cooler to a temperature sufficiently low to substantially eliminate further cooling of the expiration air as it passes through the expiration air flow path of the expiration air means and through the flow transducer means;

e. passing the expiration air to and through the expiration air flow path of the expiration air means and through said flow transducer means;

f. measuring the linear flow rate of the expiration air as it passes through the flow transducer means; and g. initiating the delivery of subsequent inspiration air in response to the linear flow rate of the expiration air as measured with the flow transducer means.

10. The ventilating method of claim 9 in which said cooling comprises cooling the expiration air in a heat exchanger.

11. The ventilating method of claim 9 and which includes prior to step e. the step of filtering the expiration air.

12. The ventilating method of claim 9 in which said cooling of step d. comprises cooling the expiration air greater than about 10° F.

13. The ventilating method of claim 9 in which said cooling of step d. comprises cooling the expiration air to not more than about 5° F. above ambient temperature.

14. The ventilating method of claim 13 in which said cooling of step d. comprises cooling the expiration air to below ambient temperature.

15. The ventilating method of claim 9 in which the temperature within the air flow path is at a first temperature, and in which said cooling of step d. comprises cooling the expiration air to not more than about 2° F. above the first temperature.

16. The ventilating method of claim 15 in which said cooling of step d. comprises cooling the expiration air to below the first temperature.

17. A ventilating system for providing inspiration air to a patient and for receiving expiration air from the patient, which comprises:

a volume-cycled ventilator apparatus having inspiration air means and expiration air means, the inspiration air means being for providing inspiration air for delivery to the patient, the expiration air means being for receiving the expiration air from the patient, the expiration air means including an expiration air flow path within said ventilator apparatus;

flow transducer means located within the expiration air flow path for receiving the expiration air therethrough and for measuring the volumetric flow rate of the expiration air passed therethrough, said flow transducer means further being for initiating the delivery of inspiration from the inspiration air means in response to the measured volumetric flow rate of the expiration air;

inspiration conduit means connecting with the inspiration air means for communicating inspiration air to the patient;

first expiration conduit means for receiving expiration air from the patient;

expiration air cooling means including an expiration air cooler and being for cooling the expiration air received from the patient, said first expiration conduit means connecting with the expiration air cooler and being for communicating expiration air from the patient to the expiration air cooler; and second expiration air conduit means communicating between the expiration air cooler and the expiration air means of said ventilator apparatus for delivering air from the expiration air cooler to and through the expiration air flow path of the expiration air means and through said flow transducer means;

said expiration air cooling means being for cooling the expiration air to a temperature sufficiently low to substantially eliminate further cooling of the expiration air as it passes through the expiration air flow path of the expiration air means and through said flow transducer means.

said flow transducer means thereby receiving the expiration air therethrough, measuring the volumetric flow rate of the expiration air passing therethrough, and initiating the delivery of subsequent inspiration air in response to the measured volumetric flow rate of the expiration air.

18. The ventilating system of claim 17 in which said expiration air cooling means comprises a heat exchanger.

19. The ventilating system of claim 17 in which said second expiration air conduit means includes an air filter.

20. The ventilating system of claim 17 in which said expiration air cooling means is for cooling the expiration air greater than about 10° F.

21. The ventilating system of claim 17 in which said expiration air cooling means is for cooling the expiration air to not more than about 5° F. above ambient temperature.

22. The ventilating system of claim 21 in which said expiration air cooling means is for cooling the expiration air to below ambient temperature.

23. The ventilating system of claim 17 in which the temperature within the air flow path of the expiration air means of said ventilator apparatus is at a first temperature, and in which said expiration air cooling means is for cooling the expiration air to not more than about 2° F. above the first temperature.

24. The ventilating system of claim 23 in which said expiration air cooling means is for cooling the expiration air to below the first temperature.

25. A ventilating method for providing inspiration air to a patient and for receiving expiration air from the patient, which comprises the steps of:

a. providing a volume-cycled ventilator apparatus having inspiration air means and expiration air means, the inspiration air means being for providing inspiration air for delivery to the patient, the expiration air means being for receiving and detecting the expiration air from the patient, the expiration air means including an expiration air flow path within the ventilator apparatus, said ventilator apparatus further including a flow transducer means located within the expiration air flow path for receiving the expiration air therethrough and for measuring the volumetric flow rate of the expiration air passed therethrough, said flow transducer means further being for initiating the delivery of inspiration air from the inspiration air means in response to the measured volumetric flow rate of the expiration air;

b. delivering the inspiration air from the inspiration air means to the patient;

c. receiving the expiration air from the patient and delivering the expiration air to an expiration air cooler;

d. cooling the expiration air in the expiration air cooler to a temperature sufficiently low to substantially eliminate further cooling of the expiration air as it passes through the expiration air flow path of the expiration air means and through the flow transducer means;

e. passing the expiration air to and through the expiration air flow path of the expiration air means and through said flow transducer means;

f. measuring the volumetric flow rate of the expiration air as it passes through the flow transducer means; and g. initiating the delivery of subsequent inspiration air in response to the volumetric flow rate of the expiration air as measured with the flow transducer means.

26. The ventilating method of claim 25 in which said cooling comprises cooling the expiration air in a heat exchanger.

27. The ventilating method of claim 25 and which includes prior to step e. the step of filtering the expiration air.

28. The ventilating method of claim 25 in which said cooling of step d. comprises cooling the expiration air greater than about 10° F.

29. The ventilating method of claim 25 in which said cooling of step d. comprises cooling the expiration air to not more than about 5° F. above ambient temperature.

30. The ventilating method of claim 29 in which said cooling of step d. comprises cooling the expiration air to below ambient temperature.

31. The ventilating method of claim 25 in which the temperature within the air flow path is at a first temperature, and in which said cooling of step d. comprises cooling the expiration air to not more than about 2° F. above the first temperature.

32. The ventilating method of claim 31 in which said cooling of step d. comprises cooling the expiration air to below the first temperature.

\* \* \* \* \*